(12) United States Patent
Bakonyi et al.

(10) Patent No.: US 6,258,961 B1
(45) Date of Patent: Jul. 10, 2001

(54) INTERMEDIATES AND PROCESS FOR THE PREPARATION THEREOF

(75) Inventors: Mária Bakonyi, Budapest; Marianna Csatári née Nagy, Erdőkertes; Erzsébet Molnár née Bakó, Sződliget; Zoltán Makovi, Budapest; Piroska Jobb, Szentendre; Edit Bai née Tállai, Budapest, all of (HU)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/423,801

(22) PCT Filed: May 11, 1998

(86) PCT No.: PCT/HU98/00047

§ 371 Date: Nov. 12, 1999

§ 102(e) Date: Nov. 12, 1999

(87) PCT Pub. No.: WO98/51681

PCT Pub. Date: Nov. 19, 1998

(30) Foreign Application Priority Data

May 13, 1997 (HU) .............................................. P97 00884

(51) Int. Cl.$^7$ ...................................................... C07D 333/22
(52) U.S. Cl. .................................................................. 549/77
(58) Field of Search ................................................. 549/77

(56) References Cited

U.S. PATENT DOCUMENTS

| 4,847,265 | 7/1989 | Badorc et al. . | |
| 5,204,469 | * | 4/1993 | Descamps et al. ..................... 549/77 |

FOREIGN PATENT DOCUMENTS

| 0099802A1 | 2/1984 | (EP) . |
| 0274324A1 | 7/1988 | (EP) . |
| 0420706A2 | 4/1991 | (EP) . |
| 0466569A1 | 1/1992 | (EP) . |

* cited by examiner

*Primary Examiner*—Deborah C. Lambkin
(74) *Attorney, Agent, or Firm*—Birch, Stewart, Kolasch & Birch, LLP

(57) ABSTRACT

A process for the preparation of 2-[(2-thienyl)-ethylamino]-(2-halogenophenyl)-acetamides of general formula (VII) starting from the nitriles of general formula (I). Compounds of general formula (VII) are valuable intermediates.

14 Claims, 2 Drawing Sheets

(VII)

(I)

INTERMEDIATES AND PROCESS FOR THE PREPARATION THEREOF

This application is the national phase under 35 U.S.C. § 371 of PCT International Application No. PCT/HU98/00047 which has an International filing date of May 11, 1998, which designated the United States of America.

This invention relates to the new intermediates of general formula (VII), wherein X stands for halogen atom, and to the process of their preparation.

It is known that methyl (2-halogenophenyl)-(6,7-dihydro-4H-thieno[3,2-c]pyridin-5-yl)acetates and their salts can favorably be used in the treatment, first of all owing to their platelet-aggregation-inhibitory and antithrombotic effect.

An especially favorable representative of these compounds, falling under general formula (VI)—wherein X means chloro atom, is the dextrotatory methyl (+)-[(S)-(2-chlorophenyl)-(6,7-dihydro-4H-thieno[3,2-c]pyridin-5-yl) acetate hdyrogen sulfate], with the international non-proprietary name (INN) clopidogrel (European patent application, Publication Nr. 099802).

Large-scale preparation of compounds of general formula (VI), wherein X means halogen atom, was previously feasible only through the strongly lacrimatory and mucous membrane irritant α-halogenophenylacetic acid derivatives, which are difficult to handle and are unfavourable from a health and environmental perspective. (European patent applications, Publications Nos. 099802, 0420706, 0466569). Furthermore, yields of the known methods are rather poor.

Our aim was to eliminate the use of the above unpleasant intermediates (such as for instance α-bromo-(2-chlorophenyl)acetic acid and its methyl ester) and to enhance substantially the yield of compounds of general formula (VI) in the synthesis.

In the synthesis according to our present invention, each intermediate is chiral in the preparation of an optically active end-product, as for instance clopidogrel, thus, the possibility is open to use, from the first step on, optically active compounds as intermediates. The economic benefit of the method is, among others, the avoidance of preparation of an unwanted isomer.

We have found that preparing the compounds of general formula (VI) by the route shown on scheme 1, that the use of the unpleasant intermediates can be avoided, and in addition, the yield of the synthesis is much higher. The subject of the present invention is the second section of reaction scheme 1.

The optically active compounds of general formula (VII) are prepared either from the optically active compounds of general formula (I) by the process according to our invention, or by resolving the racemic compound of general formula (VII) to its optical isomers.

According to our invention a racemic or optically active compound of general formula (I), wherein the meaning of X is as defined above, or its salts are transformed, and if desired, the resulting racemic compound of general formula (VII) is resolved to its optically active isomers, and if desired, the racemic compound or the optically active isomers are transformed into their salts, or the racemic compound or the optically active isomers are liberated from their salts.

The reaction of the compounds of general formula (I) with methanol and hydrochloric acid is performed in dry organic solvent. Alkyl acetates such as for instance methyl acetate or ethyl acetate may favorably be applied as the organic solvent. The reaction is carried out at a temperature between 0° C. and +60° C., preferably between 10° C. and 50° C. The optically active compounds of general formula (VII) are prepared either from the optically active compounds of general formula (I) by the route according to our invention, or by resolution of the racemic compound of general formula (VII). As for resolving agent numerous chiral acids may be applied, very advantageous is the application of L-(+)-tartaric acid in the presence of formic acid and isopropanol.

Preparation of the compounds of general formula (I) is demonstrated in the examples and in scheme 1. Starting materials (III), (IV) and (V) of the synthesis may be purchased, synthesis of the compound of formula (II) is described, e.g. in the French patent application publication No. 2608607.

Figure 1A:
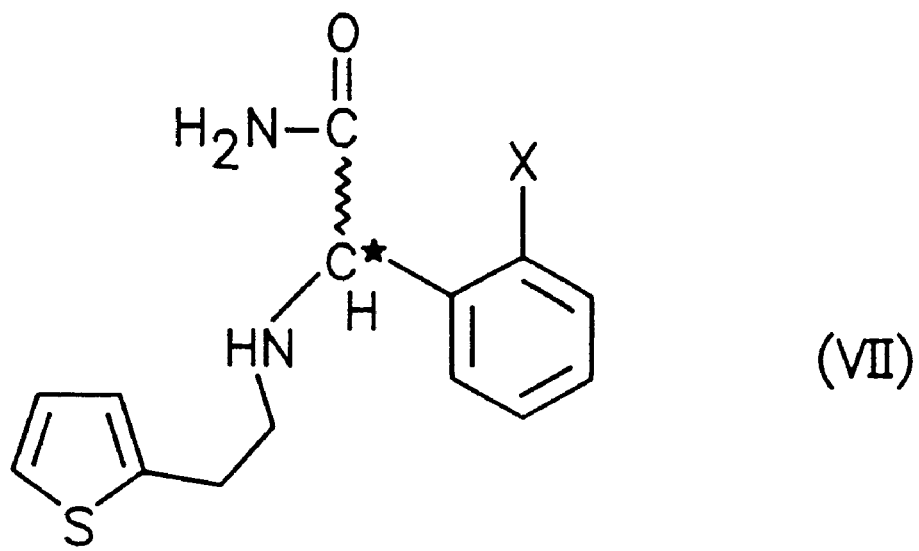
FIG. 1A is a pictorial representation of general formula (VII)
Figure 1B:
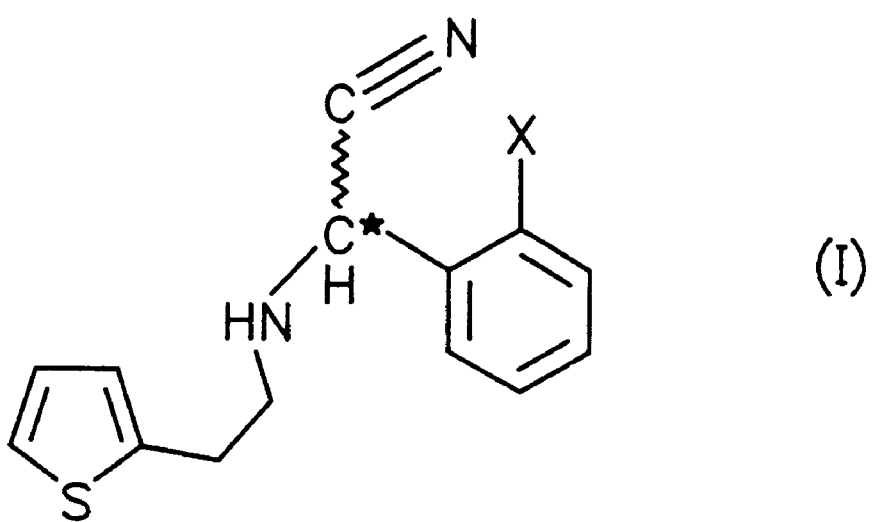
FIG. 1B is a pictorial representation of general formula (VII)
Figure 2:
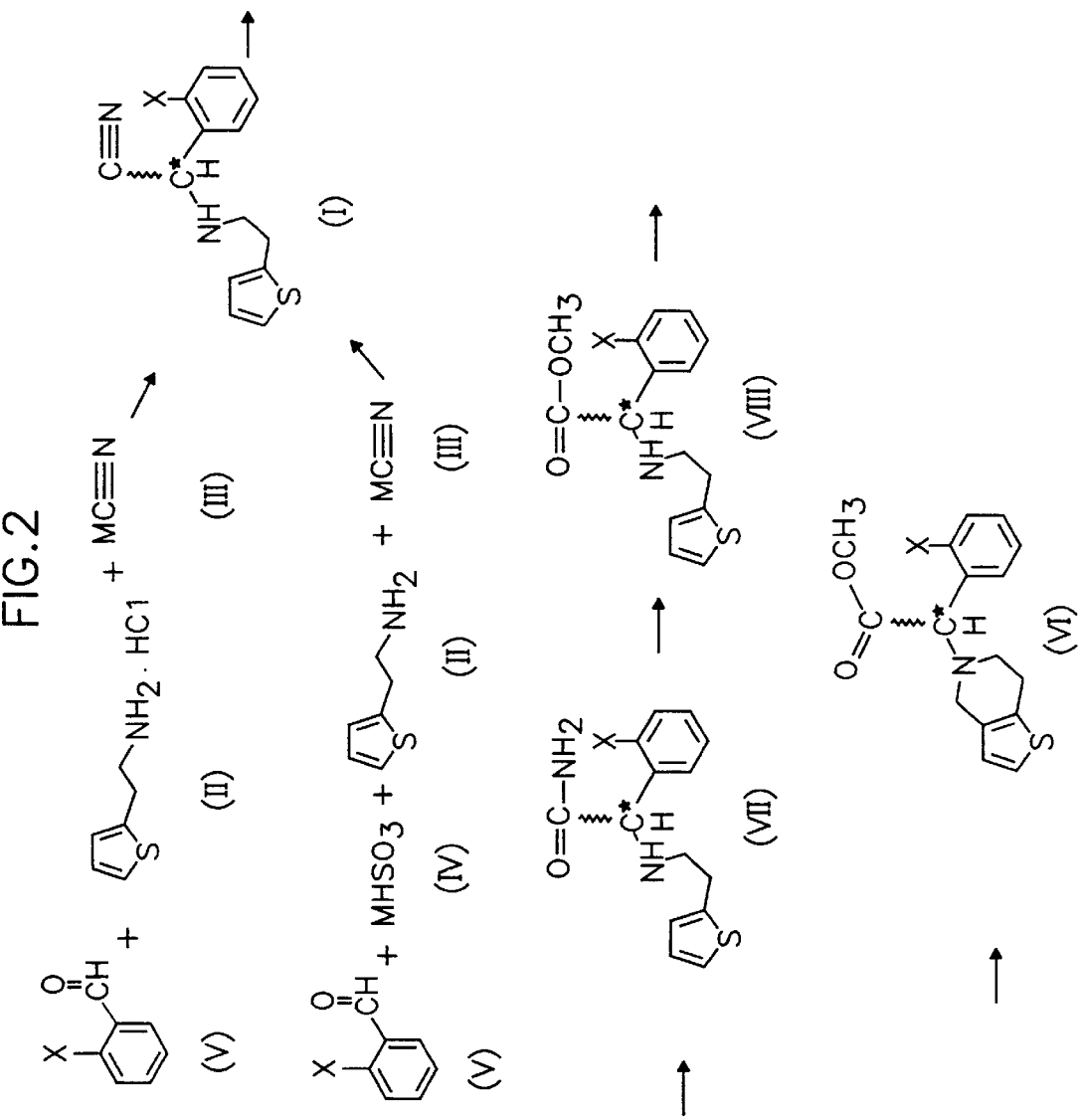
FIG. 2 is a pictorial representation of reaction scheme 1.

Further details of the invention are illustrated by the following examples, without limiting the scope of the invention to the examples.

EXAMPLE 1

[2-(2-thienyl)ethylamino](2-chlorophenyl) acetonitrile 104 g (1 mol) of sodium bisulfite is dissolved in the mixture of 900 ml of water and 250 mol of ethanol and to the solution 140.6 g (1 mol) o-chlorobenzaldehyde is added. After a few minutes the aldehyde bisulfite adduct precipitates in the form of white crystals, while the temperature increases to 40° C. After 1 hour of stirring 127.2 g (1 mol) of 2-(2-thienyl)ethylamine is added to the reaction mixture, then it was stirred at 50° C. for 2 hours. During this time the crystalline aldehyde bisulfite transforms into an oily material. The mixture is cooled to room temperature and the solution of 49 g (1 mol) of sodium cyanide in 100 ml of water is added to it. During the addition, the temperature of the reaction mixture increases to 40° C. The mixture is then stirred at 60° C. Till the reaction is completed (1 hour). The oily organic phase is then extracted with 400 ml of 1,2-dichloroethane, washed to cyanide-free with 2×200 ml of water. Traces of 2-(2-thienyl)ethylamine are removed by treatment with 100 ml of 3% hydrochloric acid solution. The dichloroethane phase was dried over anhydrous sodium sulfate and evaporated in vacuo. The residual fast crystallizing oil is the product. Weight: 260 g (94%) mp.: 40–41° C. The product was identified by elemental analysis, IR spectrum and $^1$H-NMR investigation.

EXAMPLE 2

[2-(2-thienyl)ethylamino](2-chlorophenyl) acetonitrile 9.8 g (0.2 mol) of sodium cyanide is dissolved in 70 ml of water and to the solution first 32.8 g (0.2 mol) of 2-(2-thienyl)ethylamine hydrochloride, then in a period of a few minutes, the solution of 28.2 g (0.2 mol) of o-chlorobenzaldehyde in 30 ml of ethanol are added. During the addition the temperature of the mixture increases to 45° C. The reaction mixture is then stirred at 60° C. for 2 hours, then cooled to room temperature and diluted with 50 ml of water. The resulting oily product is extracted with 100 ml of 1,2-dichloroethane. The organic phase is washed to cyanide-free with 2×50 ml of water. The traces of 2-(2-thienyl)ethylamine are removed by treatment with 20 ml of 3% hydrochloric acid solution. The residual fast crystallizing oil is the product. Weight: 52 g (94%) mp.: 40–41° C. The product was identified as written in Example 1. Quality of the product is identical with that of the product prepared according to Example 1.

EXAMPLE 3

[2-(2-thienyl)ethylamino](2-chlorophenyl)acetonitrile hydrochloride 276.7 g (1 mol) of [2-(2-thienyl)ethylamino](2-chlorphenyl)acetonitrile, prepared according to example 1 or 2, is dissolved in 600 ml of ethanol, to the solution 600 ml of 10% aqueous hydrochloric acid solution is added. Within a few minutes white crystals precipitate, then are collected, washed with 60 ml of 1:1 mixture of 10% hydrochloric acid and ethanol, then with acetone, and they are dried. Weight 305 g (97.4%), mp: 153–154° C. The product was identified by elemental analysis, IR spectrum and $^1$H-NMR investigation.

EXAMPLE 4

[2-(2-thienyl)ethylamino](2-chlorophenyl)acetonitrile hydrobromide 13.8 g (0.05 mol) of [2-(2-thienyl)ethylamino](2-chlorophenyl)acetonitrile, prepared according to example 1 or 2, is dissolved in 30 ml of ethanol, to the solution 40 ml of 20% aqueous hydrogen bromide solution is added. The product which precipitates within a few minutes is collected, washed with ethyl acetate and then they are dried. Weight: 14 g (78.2%), mp.: 144–145° C. The product was identified by elemental analysis, IR spectrum and $^1$H-NMR investigation.

EXAMPLE 5

[2-(2-thienyl)ethylamino](2-chlorophenyl)acetonitrile hydrochloride

Into 1200 ml of methyl acetate 204 g (5.6 mol) of hydrogen chloride gas is introduced at 15–25° C., and to the solution 221.4 g (0.8 mol) of the [2-(2-thienyl)ethylamino](2-chlorophenyl)acetonitrile of formula (I), prepared as described in Example 1, and 48 ml (1.2 mol) of methanol are added and the mixture is stirred at 20–25° C. for 6 hours. In the course of the reaction first the hydrochloride of the stating "nitrile", then gradually the hydrochloride of the resulting "acid amide" precipitates, in the form of white crystals. The crystals are collected by filtration, washed with methyl acetate and dried. Weight: 249 g (94%) mp.: 231–232° C.

The product was identified by elemental analysis, IR spectrum and $^1$H-NMR investigation.

EXAMPLE 6

[2-(2-Thienyl)ethylamino](2-chlorophenyl)acetonitrile hydrochloride

Into 700 ml ethyl acetate at 0–10° C. 109.8 g (3 mol) of hydrogen chloride gas was introduced and to the solution 83 g (0.3 mol) of the [2-(2-thienyl)ethylamino](2-chlorophenyl)acetonitrile of formula (I), prepared according to Example 1 or 2, and 15 ml (0.37 mol) of methanol are added and the mixture is slowly, in a period of 20 minutes, heated to 45–50° C. the reaction mixture is then stirred at 45–50° C. for 4 hours, the crystalline product is filtered off at room temperature, washed with ethyl acetate and dried. Weight: 90.4 g (91%) op.: 231–232° C. The quality of the product is identical with that of the product of Example 5.

EXAMPLE 7

[2-(2-Thienyl)ethylamino](2-chlorophenyl)acetamide 24.8 g (0.075 mol) of [2-(2-thienyl)ethylamino](2-chlorophenyl)acetamide hydrochloride, prepared according to example 5 or 6, is mixed with 170 ml of water, then under mild cooling 30 ml of 10% sodium hydroxide solution and 170 ml of 1,2-dichloroethane are added. The phases are separated, the aqueous phase is extracted with 2×20 ml of 1,2-dichloroethane, the combined organic layer is evaporated in vacuo. Residue: 22 g, fast crystallizing oil. The raw product is recrystallized from 80 ml of isopropyl acetate to give 19.5 g of the crystalline base of formula (VII). Yield: 88.2%, mp.: 90–92° C.

The product was identified by elemental analysis, IR spectrum and $^1$H-NMR investigation.

EXAMPLE 8

[2-(2-thienyl)ethylamino](2-chlorophenyl)acetamide hydrobromide 14.7 g (0.05 mol) of [2-(2-thienyl)ethylamino](2-chlorophenyl)acetamide, prepared as described in Example 7, is dissolve din 150 ml of acetone. To the solution 4 ml of 60% aqueous hydrogen bromide solution is added and the precipitated white crystals are filtered off, washed with acetone and dried.

The product was identified by elemental analysis, IR spectrum and $^1$H-NMR investigation.

EXAMPLE 9

Methyl [2-(2-thienyl)ethylamino](2-chlorophenyl)acetate hydrochloride 21.5 ml (0.4 mol) of 100% sulfuric acid is dissolved, under cooling in 100 ml of methanol, the solution is heated under reflux for ½ hour, then cooled to room temperature and to it 33.1 g (0.1 mol) of [2-(2-thienyl)ethylamino](2-chlorophenyl)acetamide hydrochloride, prepared as described in Example 5, is added and the mixture is heated under reflux conditions for 10 hours. Methanol is then distilled off in vacuo and to the residue 150 ml of 1,2-dichloroethane and 150 ml of water are added, shaken well, and the two phases are separated. The aqueous layer is extracted with 2×30 ml of 1,2-dichloroethane, the combined organic layers are washed with 80 ml of 5% sodium hydroxide solution, then with 100 ml of water, dried over anhydrous sodium sulfate and evaporated in vacuo. Weight of the residue: 28.5 g. The oily product, which is the base of formula (VIII), is dissolved in 50 ml of isopropyl acetate, 7.3 ml (0.087 mol) of concentrated hydrochloric acid solution is added to it, and the mixture is stirred at room temperature for 1 hour. The precipitating product is filtered off, washed with 2×10 ml of isopropyl acetate and dried. Weight: 28.4 g (82%) mp.: 177–178° C. (lit. 175° C.).

The product was identified by elemental analysis, IR spectrum, $^1$H-NMR and MS investigation and mp determination.

EXAMPLE 10

Methyl[2-(2-thienyl)ethylamino](2-chlorophenyl)
acetate hydrochloride

In 150 ml of methanol 8.5 ml (0.15 mol) of 96% sulfuric acid is dissolved under cooling and the solution is then heated under reflux conditions for ½ hour. After cooling to room temperature 20 g (0.0678 mol) of [2-(2-thienyl) ethylamino](2-chlorophenyl)acetamide, falling under general formula (VII) and prepared as described in Example 7, is added to the solution, the mixture is placed into a closed apparatus (autoclave) and stirred at 130° C.—on for 5 hours, while the inner pressure elevates to 13 bar. The reaction mixture is then cooled to room temperature (remaining pressure 1–2 bar), the methanol is distilled off in vacuo and to the residue 100 ml of isopropyl acetate and 100 ml of water are added and the pH of the mixture is adjusted to 7.5 by dropwise addition of 60 ml of 10% sodium hydroxide solution, under cooling and stirring, while keeping the mixture at room temperature. The phases are separated, the organic phase is stirred with 60 ml of 3% aqueous maleic acid solution at 40–50° C. for 10 minutes, the two phases are then separated. After re-extracting the aqueous maleic acid solution with 30 ml so isopropyl acetate the organic layers are combined, dried over anhydrous sodium sulfate and concentrated to the half of its volume. On addition of 5 ml of conc. hydrochloric acid solution the product precipitates as an oil which crystallizes within a few minutes. It is cooled to 0–(+5)° C. and after 2 hours the crystals are collected by filtration, washed with a small amount of isopropyl acetate and dried. Weight: 19.4 g (82.5%) mp.: 177–178° C. The quality of the product is similar to that of the material obtained in Example 9.

EXAMPLE 11

Methyl [2-(2-thienyl)ethylamino](2-chlorophenyl)
acetate hydrobromide

The procedure as describe din Example 9 is followed, the resulting methyl [2-(2-thienyl)ethylamino](2-chlorophenyl) acetate is dissolved in 50 ml of isopropyl acetate, to the solution 8 ml of 62% aqueous hydrogen bromide solution is added and the mixture is stirred at room temperature for 1 hour. During this time the product crystallizes. The crystals are collected, washed with 2×10 ml of isopropyl acetate and dried. Weight: 32.5 g (83%) mp.: 164–165° C. The product was identified by elemental analysis, IR spectrum and $^1$H-NMR investigation.

EXAMPLE 12

Methyl(2-chlorophenyl)(6,7-dihydro-4H-thieno[3,2-
c]pyridin-5-yl)acetate hydrochloride hydrate To 28.4 g (0.082 mol) of methyl [2-(2-thienyl) ethylamino](2-chlorophenyl)acetate hydrochloride, prepared according to example 9 or 10, are added 50 ml of 1,2-dichloroethane and the solution of 7.5 g (0.09 mol) of sodium hydrogen carbonate in 100 ml of water. The mixture is stirred well, the phases are separated, the aqueous phase is washed with 2×30 ml of 1,2-dichloroethane, the combined organic layer is dried over anhydrous sodium sulfate and the solvent is removed in vacuo. The residual 25 g material (acetate base) is dissolve din 90 ml of formic acid, to the solution 4 g (0.13 mol) of para formaldehyde is added and the mixture is stirred at 50° C. for 20 minutes. The majority of the formic acid is then distilled off in vacuo, the residue is dissolved in the mixture of 100 ml of water and 100 ml of 1,2-dichloroethane, the phases are separated, the aqueous phase is extracted again with 30 ml of 1,2-dichloroethane, the combined organic phase is shaken well with 100 ml of 5% sodium hdyrogen carbonate solution, the phases are separated and the organic phase is dried over anhydrous sodium sulfate and evaporated in vacuo. The residue is dissolved in 45 ml of acetone and to the solution 6.5 ml (0.077 mol) of conc. hydrochloric acid is added at 5–10° C., under cooling. The product slowly crystallizes. The mixture is stirred for 1 hour at 0–10° C., then the crystals are filtered off, washed with 2×10 ml of acetone and dried. Weight: 26.7 g (theoretical: 30.8 g ) Yield: 86.6%, mp.: 138–140° C. (literature mp: 130–140° C.). The product was identified by elemental analysis, IR spectrum, $^1$H-NMR investigation and melting point determination.

EXAMPLE 13

Laevorotatory [2-(2-thienyl)ethylamino](2-
chlorophenyl)acetonitrile hydrochloride 10 g (0.036 mol) of racemic [2-(2-thienyl)ethylamino](2-chlorophenyl)acetonitrile (I) is dissolved in 15 ml of acetone, to the solution 10 g (0.043 mol) of (1R)-(–)-camphor-10-sulfonic acid and 0.5 ml (0.013 mol) of formic acid are added, the mixture is heated to 50–55° C., then after 1–2 minutes it is cooled to room temperature. Thus gradually precipitates the salt formed between the dextrorotatory enantiomer of the starting material and (1R)-(–)-camphor-10-sulfonic acid, in an optically slightly contaiminated form. The crystals are separated by filtration. To the mother liquor 7 ml of methyl acetate containing 10% hydrogen chloride is added, or calculated amount of dry hdyrogen chloride gas is introduced, the crystalline precipitate is filtered off, washed with acetone and dried. Weight: 2.5 g $[\alpha]^{22}_D=-43°$ (c=1, methanol). Yield: 43%, calculated on the laevarotatory enantiomer content of the starting material.

After recrystallization from ethanol: $[\alpha]^{22}_D=-48°$ (c=1, methanol). Mp: 151–152° C. (decomposition). Optical purity<98% (determined by HPLC investigation).

The product was identified by elemental analysis, IR spectrum and $^1$H-NMR investigation.

EXAMPLE 14

Dextrorotatory [2-(2-thienyl)ethylamino](2-
chlorophenyl)acetonitrile hydrochloride The procedure described in the previous example is followed, but as resolving acid (1S)-(+)-camphor-10-sulfonic acid is applied. Product: weight 2.5 g, $[\alpha]^{22}_D=+43°$ (c=1, methanol). Yield: 43%, calculated on the dextrorotatory enantiomer content of the starting material. After recrystallization from ethanol: $[\alpha]^{22}_D=+48°$ (c=1, methanol). Mp.: 151–152° C. (decomposition). Optical purity>98% (determined by HPLC investigation).

The product was identified by elemental analysis, IR spectrum and $^1$H-NMR investigation.

EXAMPLE 15

Dextrorotatory [2-(2-thienyl)ethylamino](2-
chlorophenyl)acetamide 11.8 g (0.037 mol) of laevorotatory [2-(2-thienyl) ethylamino](2-chlorophenyl)acetonitrile hydrochloride is suspended in 100 ml of methyl acetate and 9.6 g of dry hydrogen chloride gas is introduced at room temperature.

Following this 3.6 g (0.113 mol) of methanol is added and the mixture is stirred room temperature until the reaction is completed 6 hours. The precipitated crystalline material, the hydrochloride salt of the product, is then filtered off, suspended in water, neutralized with sodium hydrogen carbonate, under stirring. The precipitated white crystalline raw product is filtered off, dried and recrystallized from ethanol Weight 5 g, $[\alpha]^{22}_D$=+63° (c=1, methanol). Mp.: 122–124° C. yield: 46%. Optical purity 97%.

The product was identified by elemental analysis, IR spectrum and $^1$H-NMR investigation.

EXAMPLE 16

Dextrorotatory [2-(2-thienyl)ethylamino](2-chlorophenyl)acetamide 38 g (0.129 mol) of racemic [2-(2-thienyl)ethylamino](2-chlorophenyl)acetamide is dissolved at 50° C. in 380 ml of isopropanol containing 0–0.4% advantageously 0.2% of water and to this solution is added the 50° C. solution of 10.6 g (0.071 mol) of L(+)-tartaric acid in 230 ml of isopropanol, containing 0–0.4%, advantageously 0.2% of water. The mixture is stirred at 50° C. for 30 minutes. Thick, white precipitate is formed. To the mixture 3.4 ml (0.09 mol) of formic acid is added and stirring is continued at 50° C. for 1 hour. The reaction mixture is then cooled to room temperature, stirred for another hour and the solid phase is filtered off. The precipitated material is the salt formed between the laevorotatory enantiomer of the starting material and L(+)-tartaric acid, in an optically slightly contaminated form. Weight: 30 g Mp.: 167–169° C., after crystallization form ethanol. The mother liquor is evaporated in vacuo. The residue (29 g) is taken up in 200 ml of water and 200 ml of 1,2-dichloroethane and neutralized under stirring with 16 g (0.19 mol) of sodium hydrogen carbonate. The phases are separated, the aqueous layer is washed with 2×30 ml of 1,2-dichloroethane, the combined organic layer is extracted with 50 ml of water, dried over anhydrous sodium sulfate and evaporated in vacuo. Weight: 18 g. The raw product is recrystallized from 70 ml of ethanol, washed with a small amount of ethanol and dried. Weight: 12.6 g Mp.: 122–124° C., $[\alpha]^{22}_D$=+69° (c=1, methanol). Yield: 66.3% calculated on the dextrorotatory enantiomer content of the starting material. Optical purity: 99–100%, usually higher than 98% (determined by HPLCO).

The product was identified by elemental analysis, IR spectrum and $^1$H-NMR investigation.

By concentration of the filtrate 4 g of racemic starting material can be recovered.

EXAMPLE 17

Dextrorotatory [2-(2-thienyl)ethylamino](2-chlorophenyl)acetamide 76 g (0.257 mol) of racemic [2-(2-thienyl)ethylamino](2-chlorophenyl)acetamide is dissolved at 50° C. in 1200 ml of isopropanol containing 0.2% of water and to this solution 21.2 g (0.141 mol) of L(+)-tartaric acid and 8.3 g (0.18 mol) of formic acid are added. The mixture is stirred at 50° C. for 1 hour while thick white precipitate is formed. The reaction mixture is then cooled to room temperature during a period of 1 hour, stirred for another 2 hours and the solid phase is filtered off.

The precipitated material is the salt formed between the laevorotatory enantiomer of the starting material and L(+)-tartaric acid is an optically slightly contaminated form. Weight: 57 g Mp.: 167–169° C. after crystallization from ethanol. After filtration of the former solid material 5.2 g (0.141 mol) hydrochloric acid gas is introduced into the filtrate to precipitate the hydrochloride of the product. The formed white crystallized material is filtered out and dried. Weight: 41.7 g. The obtained optically slightly contaminated salt is taken up in 100 ml of ethanol and 5.3 g (0.13 mol) of sodium hydroxide dissolved in 70 ml of ethanol is added into it gradually to release the free base. The formed product containing some sodium chloride is filtered off and washed with distilled water. After drying its weight is 27.7 g, 73% of the dextrorotatory enantiomer content of the starting material. Mp.: 122–124° C., $[\alpha]^{22}_D$=+69° (c=1, methanol).

If the ethanolic filtrate is evaporated in vacuo and the remains is taken up in water, 9 g of racemic starting material is recovered.

EXAMPLE 18

Dextrorotatory methyl[2-(2-thienyl)ethylamino](2-chlorophenyl)acetate-hydrochloride In 40 ml of methanol under cooling 11.5 ml (0.215 mol) of 100% sulfuric acid is dissolved, the solution is heated under reflux conditions for 30 minutes, then after cooling to room temperature 12.4 g (0.042 mol) of dextrorotatory [2-(2-thienyl)ethylamino](2-chlorophenyl)acetamide is added and the mixture is heated under reflux for 6–7 hours, till the end of the reaction. Methanol is distilled off in vacuo, to the residue 75 ml of 1,2-dichloroethane and 75 ml of water are added, the mixture is shaken well and the phases are separated. The aqueous phase is extracted with 2×20 ml of 1,2-dichloroethane, the united organic phase is extracted with 50 ml of 5% sodium hydroxide solution then with 50 ml of water, dried over anhydrous sodium sulfate. The drying material is filtered off and 1.5 g (0.041 mol of dry hydrogen chloride gas is introduced under cooling into the solution. The precipitated crystalline product is filtered off, washed with 1,2-dichloroethane and dried. Weight: 12.1 g, mp.: 185–186° C. (decomposition), $[\alpha]^{22}_D$=+107° . Yield: 83%. Optical purity: in general 99–100%.

The product was identified by elemental analysis, IR spectrum and $^1$H-NMR investigation.

EXAMPLE 19

Dextrorotatory methyl α-(2-thienyl)ethylamino) (2-chlorophenyl)acetate through the resolution of the racemate a) 175 g of the hydrochloride salt of compound of general formula (VIII)—wherein X means chloro atom—is dissolved in the mixture of 0.75 liter of dichloroethane and 0.25 liter of water, and to the solution, 45 g of sodium hydrogen carbonate is gradually added. After mixing, the organic phase is separated by decantation. Following the usual work-up procedure the amino-ester is obtained, which is then dissolved in 850 ml of acetone, and to the solution 87 g (+)-camphor-10-sulfonic acid is added. The mixture is kept at room temperature for 12 hours and the resulting precipitate is separated. Thus 146.5 g of camphorsulfonate is obtained, $[\alpha]^{22}_D$=+51.7° (c=1, methanol). The camphorsulfonate is suspended in 700 ml of acetone while heating under reflux conditions, and to achieve full dissolution 300 ml of methyl ethyl ketone is added. The mixture is allowed to cool down to room temperature. The resulting precipitate is separated and treated at room temperature with 500 ml of acetone and 300 ml of methyl ethyl ketone. Thus 95 g of the (+)-camphorsulfonate of the expected product is obtained, melting point: 95° C., $[\alpha]^{22}_D=+82°$ (c=1, methanol).

b) 33.5 g of the hydrochloride salt of the compound of general formula (VIII)—wherein X means chloro atom—and 14,6 g (+)-tartaric acid are mixed in 500 ml of isopropanol, heated to 50° C., then allowed to stay at room temperature. The resulting precipitate is separated and crystallized four times from isopropanol. Thus, the (+)-tartarate of the desired dextrorotatory product is obtained, melting point: 105° C. Specific rotation of the amine $[\alpha]^{20}_D=+99.76°$ (c=1, methanol).

EXAMPLE 20

Laevorotatory α-(2-thienyl)ethylamino) (2-chlorophenyl)acetic acid methyl ester through resolution of the racemate 100 g of the racemate hydrochloride of compound of general formula (VIII)—wherein X means chloro atom—and 30 g of sodium hdyrogen carbonate are mixed in 500 ml of dichloromethane and 200 ml of water. After stirring the organic phase is separated by decantation, and the solvent is distilled off in vacuo. The residue is dissolved in 800 ml of acetone and to this solution 53.3 g of (−)-camphor-10-sulfonic acid is added. The mixture is allowed to stay at room temperature of 12 hours. The resulting precipitate is separated and suspended in 300 ml of acetone. The insoluble solid precipitate is crystallized from the mixture of 600 ml of acetone and 160 ml of methyl ethyl ketone to obtained 52.5 of the (−)-camphorsulfonate of the desired product, melting point: 95° C., $[\alpha]^{22}_D=-82°$ (c=1, methanol).

EXAMPLE 21

(+)-(S)-(2-chlorophenyl(6,7-dihydro-4H-thieno[3,2-c]pyridin-5-yl)acetic acid methyl ester hdyrochloride salt 6 g (0.017 mol) of dextrorotatory methyl [2-(2-thienyl) ethylamino](2-chlorophenyl)acetate hydrochloride is suspended in 6.7 ml of 38% aqueous formaline solution and heated to 60° C. under stirring. The starting material dissolves at 60° C., the resulting solution is stirred at the temperature for 30 minutes, till the completion of the reaction. The reaction mixture is then diluted with 100 ml of 1.2 dichloroethane and 150 ml of water, and after shaking well, the phases are separated. The aqueous phase is extracted with 2×30 ml of 1,2-dichloroethane, the united organic phase is extracted with 100 ml of water, dried over anhydrous sodium sulfate, filtered and evaporated in vacuo. The residual 6 g of material is dissolved in 30 ml of diethyl ether, and while cooling the reaction mixture, 0.6 g of dry hdyrogen chloride gas is introduced into the solution, at room temperature. The precipitated crystalline material is filtered off, washed with ether and dried. Weight: 5.5 g. Mp.: 130–132° C., $[\alpha]^{22}_D=+60°$. Yield: 90.1%. Optical purity: 99% (by HPLC investigation).

EXAMPLE 22 a) (+)-(2-chlorophenyl(6,7-dihydro-4H-thieno[3,2-c] pyridin-5-yl)acetic acid methyl ester (−)-camphorsulfonic acid salt 32 g (0.0994 mol) of (2-chlorophenyl(6,7-dihydro-4H-thieno[3,2-c]pyridin-5-yl)acetic acid methyl ester is dissolved in 150 ml of acetone and to the solution 9.95 g (0.0397 mol) of laevorotatory 10-camphorsulfonic acid monohydrate is added. The homogenous reaction mixture is allowed to stay at room temperature. After 48 hours a few crystals appear. The mixture is concentrated by evaporation to 50 ml and allowed to stay at room temperature for 24 hours. The resulting crystals are filtered off, washed with acetone and dried. The crystals thus obtained are dissolved again in a very small amount (50 ml) of hot acetone and after cooling the crystals are filtered off, washed with acetone and dried. Thus the title compound is obtained. Yield: 88%. Mp.: 165° C. $[\alpha]^{20}_D=+24°$ (c=1.68 g/100 ml: methanol).

b) (+)-(2-chlorophenyl(6,7-dihydro-4H-thieno[3,2-c] pyridin-5-yl)acetic acid methyl ester To the suspension made of 200 g of (+)-(2-chlorophenyl (6,7-dihydro-4H-thieno[3,2-c]pyridin-5-yl)acetic acid methyl ester (−)-camphorsulfonic acid salt and 800 ml of dichloromethane is added 800 ml of sodium hydrogen carbonate solution. After stirring the organic phase is separated by decantation, dried on sodium sulfate and the solvent is removed in vacuo. The (+)-(2-chlorophenyl(6,7-dihydro-4H-thieno[3,2-c]pyridin-5-yl)acetic acid methyl ester is obtained as a solution in 800 ml of dichloromethane. After stirring, the organic phase is separated by decantation, dried over sodium sulfate and the solvent is removed in vacuo.

The (+)-(2-chlorophenyl)(6,7-dihydro-4H-thieno[3,2-c] pyridin-5-yl)acetic acid methyl ester is obtained in the form of colourless oil c) (+)-(2-chlorophenyl)(6,7-dihydro-4H-thieno[3,2-c]pyridin-5-yl)acetic acid methyl ester hydrogen sulfate salt The residue obtained in the previous example is dissolve din 500 ml of ice-cold acetone and to this solution 20.7 ml of concentrated sulfuric acid (93.64%; density 1.83) is added dropwise. The resulting precipitate is separated by filtration, washed with 1000 ml of acetone and dried in a vacuo oven at 50° C. Thus 139 g of the title salt is obtained in the form of white crystals. Mp.: 184° C., $[\alpha]^{20}_D=+55.1°$ (c=1.891 g/100 ml; methanol).

What is claimed is:

1. Compounds of general formula (VII)

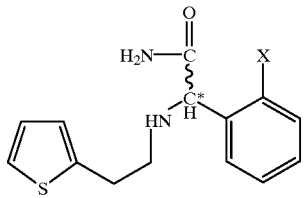

(VII)

wherein the meaning of X is halogen atom—and their optical isomers and salts.

2. Laevorotatory optical isomers of compounds of general formula (VII)—wherein the meaning of X is halogen atom—and their salts.

3. Dextrorotatory optical isomers of compounds of general formula (VII)—wherein the meaning of X is halogen atom—and their salts.

4. (+)-[2-(2-thienyl)ethylamino]-(2-chlorophenyl) acetamide and its salts.

5. (−)-[2-(2-thienyl)ethylamino]-(2-chlorophenyl) acetamide and its salts.

6. (+)-[2-(2-thienyl)ethylamino]-(2-chlorophenyl) acetamide and its salts.

7. (+)-[2-(2-thienyl)ethylamino]-(2-chlorophenyl)acetamide hydrogen chloride.

8. (−)-[2-(2-thienyl)ethylamino]-(2-chlorophenyl)acetamide hydrogen chloride.

9. Process for the preparation of compounds of general formula (VII),—wherein the meaning of X is halogen atom—characterized in that, a racemic or optically active compound of general formula (I)—wherein the meaning of X is as defined above—or their salts are transformed, and if desired, the resulting racemic compound of general formula (VII) is resolved to its optical isomers, and if desired, the racemic compound or its optical isomers are transformed into their salts, or the racemic compound or its optical isomers are liberated from their salts.

10. The process defined in claim 9, characterized in that, the compounds of general formula (I) are reacted with methanol and hydrochloric acid.

11. The process defined in claim 9, characterized in that, the reaction is carried out at a temperature between 0° C. and +60° C.

12. The process defined in claim 9, characterized in that, as organic solvent methyl acetate or ethyl acetate is used.

13. The process defined in claim 9, characterized in that, the compound of general formula (I) is applied in the form of its slat.

14. The process defined in claim 9, characterized in that, a racemic compound of general formula (VII) is resolved with L-(+)-tartaric acid, in the presence of formic acid and isopropanol.

* * * * *